United States Patent [19]

Collins

[11] Patent Number: 5,770,422
[45] Date of Patent: Jun. 23, 1998

US005770422A

[54] HUMAN TELOMERASE

[75] Inventor: Kathleen Collins, Berkeley, Calif.

[73] Assignee: The Regents of the University of California, Oakland, Calif.

[21] Appl. No.: 676,974

[22] Filed: Jul. 8, 1996

[51] Int. Cl.[6] .............................. C12N 9/12; C12N 1/20; C12N 15/00; C07H 21/04

[52] U.S. Cl. .................. 435/194; 536/23.2; 435/252.3; 435/320.1; 530/412; 530/350

[58] Field of Search .................................. 435/194, 91.1, 435/240.1, 254.11, 252.3, 320.1, 69.1, 172.3; 530/350, 412; 536/23.1, 23.2, 24.31, 24.33

[56] References Cited

U.S. PATENT DOCUMENTS 5,583,016  12/1996  Villeponteau et al. ................. 435/91.3

OTHER PUBLICATIONS

Counter et al. Proc. Natl. Acad. Sci. USA, vol. 91, pp. 2900–2904, Apr. 1, 1994.

*Primary Examiner*—Robert A. Wax
*Assistant Examiner*—Tekchand Saidha
*Attorney, Agent, or Firm*—Richard Aron Osman

[57] ABSTRACT

The invention provides methods and compositions rel a human telomerase and related nucleic acids, including four distinct human telomerase subunit proteins called p140, p105, p48 and p43 having human telomerase-specific activity. The proteins may be produced recombinantly from transformed host cells from the disclosed telomerase encoding nucleic acids or purified from human cells. Also included are human telomerase RNA components, as well as specific, functional derivatives thereof. The invention provides isolated telomerase hybridization probes and primers capable of specifically hybridizing with the disclosed telomerase gene, telomerase-specific binding agents such as specific antibodies, and methods of making and using the subject compositions in diagnosis, therapy and in the biopharmaceutical industry.

3 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 759 amino acids
        ( B ) TYPE: amino acid
        ( C ) STRANDEDNESS:
        ( D ) TOPOLOGY: Not Relevant ( i i ) MOLECULE TYPE: peptide ( x i ) SEQUENCE DESCRIPTION: SEQ ID NO:1:

```
Met Ala Gly Leu Thr Leu Phe Val Gly Arg Leu Pro Pro Ser Ala Arg
  1               5                  10                  15
Ser Glu Gln Leu Glu Glu Leu Phe Ser Gln Val Gly Pro Val Lys Gln
                 20                  25                  30
Cys Phe Val Val Thr Glu Lys Gly Ser Lys Ala Cys Arg Gly Phe Gly
             35                  40                  45
Tyr Val Thr Phe Ser Met Leu Glu Asp Val Gln Arg Ala Leu Lys Glu
         50                  55                  60
Ile Thr Thr Phe Glu Gly Cys Lys Ile Asn Val Thr Val Ala Lys Lys
 65                  70                  75                  80
Lys Leu Arg Asn Lys Thr Lys Glu Lys Gly Lys Asn Glu Asn Ser Glu
                 85                  90                  95
Cys Pro Lys Lys Glu Pro Lys Ala Lys Lys Ala Lys Val Ala Asp Lys
            100                 105                 110
Lys Ala Arg Leu Ile Ile Arg Asn Leu Ser Phe Lys Cys Ser Glu Asp
            115                 120                 125
Asp Leu Lys Thr Val Phe Ala Gln Phe Gly Ala Val Leu Glu Val Asn
        130                 135                 140
Ile Pro Arg Lys Pro Asp Gly Lys Met Arg Gly Phe Gly Phe Val Gln
145                 150                 155                 160
Phe Lys Asn Leu Leu Glu Ala Gly Lys Ala Leu Lys Gly Met Asn Met
                165                 170                 175
Lys Glu Ile Lys Gly Arg Thr Val Ala Val Asp Trp Ala Val Ala Lys
            180                 185                 190
Asp Lys Tyr Lys Asp Thr Gln Ser Val Ser Ala Ile Gly Glu Glu Lys
            195                 200                 205
Ser His Glu Ser Lys His Gln Glu Ser Val Lys Lys Lys Gly Arg Glu
        210                 215                 220
Glu Glu Asp Met Glu Glu Glu Asn Asp Asp Asp Asp Asp Asp Asp Asp
225                 230                 235                 240
Asp Glu Glu Asp Gly Val Phe Asp Asp Glu Asp Glu Glu Glu Glu Asn
                245                 250                 255
Ile Glu Ser Lys Val Thr Lys Pro Val Gln Ile Gln Lys Arg Ala Val
            260                 265                 270
Lys Arg Pro Ala Pro Ala Lys Ser Ser Asp His Ser Glu Glu Asp Ser
            275                 280                 285
Asp Leu Glu Glu Ser Asp Ser Ile Asp Asp Gly Glu Glu Leu Ala Gln
        290                 295                 300
Ser Asp Thr Ser Thr Glu Glu Gln Glu Asp Lys Ala Val Gln Val Ser
305                 310                 315                 320
```

-continued

```
Asn  Lys  Lys  Lys  Arg  Lys  Leu  Pro  Ser  Asp  Val  Asn  Glu  Gly  Lys  Thr
               325            330                      335
Val  Phe  Ile  Arg  Asn  Leu  Ser  Phe  Asp  Ser  Glu  Glu  Glu  Glu  Leu  Gly
               340            345                      350
Glu  Leu  Leu  Gln  Gln  Phe  Gly  Glu  Leu  Lys  Tyr  Val  Arg  Ile  Val  Leu
          355            360                      365
His  Pro  Asp  Thr  Glu  His  Ser  Lys  Gly  Cys  Ala  Phe  Ala  Gln  Phe  Met
          370            375                      380
Thr  Gln  Glu  Ala  Ala  Gln  Lys  Cys  Leu  Leu  Ala  Ala  Ser  Pro  Glu  Asn
385                 390                 395                           400
Glu  Ala  Gly  Gly  Leu  Lys  Leu  Asp  Gly  Arg  Gln  Leu  Lys  Val  Asp  Leu
               405                 410                      415
Ala  Val  Thr  Arg  Asp  Glu  Ala  Ala  Lys  Leu  Gln  Thr  Thr  Lys  Val  Lys
               420                 425                      430
Lys  Pro  Thr  Gly  Thr  Arg  Asn  Leu  Tyr  Leu  Ala  Arg  Glu  Gly  Leu  Ile
               435            440                      445
Arg  Ala  Gly  Thr  Lys  Ala  Ala  Glu  Gly  Val  Ser  Ala  Ala  Asp  Met  Ala
          450            455                      460
Lys  Arg  Glu  Arg  Phe  Glu  Leu  Leu  Lys  His  Gln  Lys  Leu  Lys  Asp  Gln
465                 470                 475                           480
Asn  Ile  Phe  Val  Ser  Arg  Thr  Arg  Leu  Cys  Leu  His  Asn  Leu  Pro  Lys
               485                 490                      495
Ala  Val  Asp  Asp  Lys  Gln  Leu  Arg  Lys  Leu  Leu  Leu  Ser  Ala  Thr  Ser
               500                 505                      510
Gly  Glu  Lys  Gly  Val  Arg  Ile  Lys  Glu  Cys  Arg  Val  Met  Arg  Asp  Leu
          515            520                      525
Lys  Gly  Val  His  Gly  Asn  Met  Lys  Gly  Gln  Ser  Leu  Gly  Tyr  Ala  Phe
          530            535                      540
Ala  Glu  Phe  Gln  Glu  His  Glu  His  Ala  Leu  Lys  Ala  Leu  Arg  Leu  Ile
545                 550                 555                           560
Asn  Asn  Asn  Pro  Glu  Ile  Phe  Gly  Pro  Leu  Lys  Arg  Pro  Ile  Val  Glu
               565                 570                      575
Phe  Ser  Leu  Glu  Asp  Arg  Arg  Lys  Leu  Lys  Met  Lys  Glu  Leu  Arg  Ile
               580                 585                      590
Gln  Arg  Ser  Leu  Gln  Lys  Met  Arg  Ser  Lys  Pro  Ala  Thr  Gly  Glu  Pro
          595            600                      605
Gln  Lys  Gly  Gln  Pro  Glu  Pro  Ala  Lys  Asp  Gln  Gln  Gln  Lys  Ala  Ala
          610            615                      620
Gln  His  His  Thr  Glu  Glu  Gln  Ser  Lys  Val  Pro  Pro  Glu  Gln  Lys  Arg
625                 630                 635                           640
Lys  Ala  Gly  Ser  Thr  Ser  Trp  Thr  Gly  Phe  Gln  Thr  Lys  Ala  Glu  Val
               645            650                      655
Glu  Gln  Val  Glu  Leu  Pro  Asp  Gly  Lys  Lys  Arg  Arg  Lys  Val  Leu  Ala
               660            665                      670
Leu  Pro  Ser  His  Arg  Gly  Pro  Lys  Ile  Arg  Leu  Arg  Asp  Lys  Gly  Lys
               675            680                      685
Val  Lys  Pro  Val  His  Pro  Lys  Lys  Pro  Lys  Pro  Gln  Ile  Asn  Gln  Trp
          690            695                      700
Lys  Gln  Glu  Lys  Gln  Gln  Leu  Ser  Ser  Glu  Gln  Val  Ser  Arg  Lys  Lys
705                 710                 715                           720
Ala  Lys  Gly  Asn  Lys  Thr  Glu  Thr  Arg  Phe  Asn  Gln  Leu  Val  Glu  Gln
               725                 730                      735
Tyr  Lys  Gln  Lys  Leu  Leu  Gly  Pro  Ser  Lys  Gly  Ala  Pro  Leu  Ala  Lys
               740                 745                      750
```

```
        Arg  Ser  Lys  Trp  Phe  Asp  Ser
                      755
```

(2) INFORMATION FOR SEQ ID NO:2:

(i) SEQUENCE CHARACTERISTICS:
        (A) LENGTH: 2277 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATGGCNGGNY  TNACNYTNTT  YGTNGGNMGN  YTNCCNCCNW  SNGCNMGNWS  NGARCARYTN    60
GARGARYTNT  TYWSNCARGT  NGGNCCNGTN  AARCARTGYT  TYGTNGTNAC  NGARAARGGN   120
WSNAARGCNT  GYMGNGGNTT  YGGNTAYGTN  ACNTTYWSNA  TGYTNGARGA  YGTNCARMGN   180
GCNYTNAARG  ARATHACNAC  NTTYGARGGN  TGYAARATHA  AYGTNACNGT  NGCNAARAAR   240
AARYTNMGNA  AYAARACNAA  RGARAARGGN  AARAAYGARA  AYWSNGARTG  YCCNAARAAR   300
GARCCNAARG  CNAARAARGC  NAARGTNGCN  GAYAARAARG  CNMGNYTNAT  HATHMGNAAY   360
YTNWSNTTYA  ARTGYWSNGA  RGAYGAYYTN  AARACNGTNT  TYGCNCARTT  YGGNGCNGTN   420
YTNGARGTNA  AYATHCCNMG  NAARCCNGAY  GGNAARATGM  GNGGNTTYGG  NTTYGTNCAR   480
TTYAARAAYY  TNYTNGARGC  NGGNAARGCN  YTNAARGGNA  TGAAYATGAA  RGARATHAAR   540
GGNMGNACNG  TNGCNGTNGA  YTGGGCNGTN  GCNAARGAYA  ARTAYAARGA  YACNCARWSN   600
GTNWSNGCNA  THGGNGARGA  RAARWSNCAY  GARWSNAARC  AYCARGARWS  NGTNAARAAR   660
AARGGNMGNG  ARGARGARGA  YATGGARGAR  GARGARAAYG  AYGAYGAYGA  YGAYGAYGAY   720
GAYGARGARG  AYGGNGTNTT  YGAYGAYGAR  GAYGARGARG  ARGARAAYAT  HGARWSNAAR   780
GTNACNAARC  CNGTNCARAT  HCARAARMGN  GCNGTNAARM  GNCCNGCNCC  NGCNAARWSN   840
WSNGAYCAYW  SNGARGARGA  YWSNGAYYTN  GARGARWSNG  AYWSNATHGA  YGAYGGNGAR   900
GARYTNGCNC  ARWSNGAYAC  NWSNACNGAR  GARCARGARG  AYAARGCNGT  NCARGTNWSN   960
AAYAARAARA  ARMGNAARYT  NCCNWSNGAY  GTNAAYGARG  GNAARACNGT  NTTYATHMGN  1020
AAYYTNWSNT  TYGAYWSNGA  RGARGARGAR  YTNGGNGARY  TNYTNCARCA  RTTYGGNGAR  1080
YTNAARTAYG  TNMGNATHGT  NYTNCAYCCN  GAYACNGARC  AYWSNAARGG  NTGYGCNTTY  1140
GCNCARTTYA  TGACNCARGA  RGCNGCNCAR  AARTGYYTNY  TNGCNGCNWS  NCCNGARAAY  1200
GARGCNGGNG  GNYTNAARYT  NGAYGGNMGN  CARYTNAARG  TNGAYYTNGC  NGTNACNMGN  1260
GAYGARGCNG  CNAARYTNCA  RACNACNAAR  GTNAARAARC  CNACNGGNAC  NMGNAAYYTN  1320
TAYYTNGCNM  GNGARGGNYT  NATHMGNGCN  GGNACNAARG  CNGCNGARGG  NGTNWSNGCN  1380
GCNGAYATGG  CNAARMGNGA  RMGNTTYGAR  YTNYTNAARC  AYCARAARYT  NAARGAYCAR  1440
AAYATHTTYG  TNWSNMGNAC  NMGNYTNTGY  YTNCAYAAYY  TNCCNAARGC  NGTNGAYGAY  1500
AARCARYTNM  GNAARYTNYT  NYTNWSNGCN  ACNWSNGGNG  ARAARGGNGT  NMGNATHAAR  1560
GARTGYMGNG  TNATGMGNGA  YYTNAARGGN  GTNCAYGGNA  AYATGAARGG  NCARWSNYTN  1620
GGNTAYGCNT  TYGCNGARTT  YCARGARCAY  GARCAYGCNY  TNAARGCNYT  NMGNYTNATH  1680
AAYAAYAAYC  CNGARATHTT  YGGNCCNYTN  AARMGNCCNA  THGTNGARTT  YWSNYTNGAR  1740
GAYMGNMGNA  ARYTNAARAT  GAARGARYTN  MGNATHCARM  GNWSNYTNCA  RAARATGMGN  1800
WSNAARCCNG  CNACNGGNGA  RCCNCARAAR  GGNCARCCNG  ARCCNGCNAA  RGAYCARCAR  1860
CARAARGCNG  CNCARCAYCA  YACNGARGAR  CARWSNAARG  TNCCNCCNGA  RCARAARMGN  1920
```

5,770,422

17 18

-continued

| AARGCNGGNW | SNACNWSNTG | GACNGGNTTY | CARACNAARG | CNGARGTNGA | RCARGTNGAR | 1980 |
| YTNCCNGAYG | GNAARAARMG | NMGNAARGTN | YTNGCNYTNC | CNWSNCAYMG | NGGNCCNAAR | 2040 |
| ATHMGNYTNM | GNGAYAARGG | NAARGTNAAR | CCNGTNCAYC | CNAARAARCC | NAARCCNCAR | 2100 |
| ATHAAYCART | GGAARCARGA | RAARCARCAR | YTNWSNWSNG | ARCARGTNWS | NMGNAARAAR | 2160 |
| GCNAARGGNA | AYAARACNGA | RACNMGNTTY | AAYCARYTNG | TNGARCARTA | YAARCARAAR | 2220 |
| YTNYTNGGNC | CNWSNAARGG | NGCNCCNYTN | GCNAARMGNW | SNAARTGGTT | YGAYWSN | 2277 |

( 2 ) INFORMATION FOR SEQ ID NO:3:

( i ) SEQUENCE CHARACTERISTICS:
        ( A ) LENGTH: 2733 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| TGAGCTTGGT | TGTCCTACCA | AAGCCAGCGT | TTCGGCTCGC | GTGCGCCGGC | CTAGTTTGCT | 60 |
| CGCGTCCTCA | CGCGCTTTGG | GTTTCCCGGT | CTCATGGCCG | GCCTGACCTT | ATTTGTGGGC | 120 |
| CGCCTCCCGC | CCTCGGCCCG | CAGTGAGCAG | CTGGAGGAAC | TGTTCAGTCA | GGTGGGGCCG | 180 |
| GTGAAGCAGT | GCTTCGTGGT | GACTGAAAAA | GGGAGTAAGG | CATGTCGAGG | CTTTGGCTAT | 240 |
| GTCACTTTTT | CAATGCTGGA | AGATGTTCAG | AGGGCCCTCA | AGGAGATTAC | CACCTTTGAA | 300 |
| GGTTGCAAGA | TCAACGTGAC | TGTTGCCAAG | AAAAAACTGA | GGAACAAGAC | AAAGGAAAAG | 360 |
| GGGAAAAATG | AAAACTCAGA | GTGCCCAAAG | AAGGAGCCGA | AGGCTAAAAA | AGCCAAAGTG | 420 |
| GCAGATAAGA | AAGCCAGATT | AATTATTCGG | AACCTGAGCT | TTAAGTGTTC | AGAAGATGAC | 480 |
| TTGAAGACAG | TATTTGCTCA | ATTTGGAGCT | GTCCTGGAAG | TAAATATCCC | TAGGAAACCA | 540 |
| GATGGGAAGA | TGCGCGGTTT | TGGTTTTGTT | CAGTTCAAAA | ACCTCCTAGA | AGCAGGTAAA | 600 |
| GCTCTCAAAG | GCATGAACAT | GAAAGAGATA | AAAGGCCGGA | CAGTGGCTGT | GGATTGGGCC | 660 |
| GTGGCAAAGG | ATAAATATAA | AGATACACAG | TCTGTTTCTG | CTATAGGTGA | GGAAAAGAGC | 720 |
| CATGAATCTA | ACATCAGGA | ATCAGTTAAA | AAGAAGGGCA | GAGAGGAAGA | GGATATGGAA | 780 |
| GAGGAAGAAA | ACGATGATGA | TGACGATGAT | GATGATGAAG | AAGATGGGGT | TTTTGATGAT | 840 |
| GAAGATGAAG | AGGAAGAGAA | TATAGAATCA | AAGGTGACCA | AGCCTGTGCA | AATTCAGAAG | 900 |
| AGAGCAGTCA | AGAGACCAGC | CCCTGCAAAA | AGCAGTGATC | ATTCTGAGGA | GGACAGTGAC | 960 |
| CTAGAGGAAA | GCGATAGTAT | TGATGATGGA | GAGGAACTGG | CTCAGAGTGA | TACCAGCACT | 1020 |
| GAGGAGCAAG | AGGATAAAGC | TGTGCAAGTC | TCAAACAAAA | AGAAGAGGAA | ATTACCCTCT | 1080 |
| GATGTGAATG | AAGGGAAAAC | TGTTTTTATC | AGAAATCTGT | CCTTTGACTC | AGAAGAAGAA | 1140 |
| GAACTTGGGG | AGCTTCTCCA | ACAGTTTGGA | GAACTCAAAT | ATGTCCGCAT | TGTCTTGCAT | 1200 |
| CCAGACACAG | AGCATTCTAA | AGGTTGTGCA | TTTGCCCAGT | TCATGACTCA | AGAAGCAGCT | 1260 |
| CAGAAATGCC | TTCTAGCTGC | TTCTCCAGAG | AATGAGGCTG | GTGGGCTTAA | ACTGGATGGC | 1320 |
| CGGCAGCTCA | AGGTTGACTT | GGCGGTGACC | CGTGATGAGG | CTGCAAAGCT | TCAGACGACG | 1380 |
| AAGGTGAAGA | AGCCGACTGG | CACCCGGAAT | CTCTATCTGG | CCCGAGAAGG | CTTGATTCGT | 1440 |
| GCTGGGACGA | AGGCTGCAGA | GGGTGTGAGT | GCTGCTGATA | TGGCCAAAAG | AGAACGGTTT | 1500 |
| GAGCTGCTGA | AGCATCAGAA | ACTCAAGGAC | CAGAATATCT | TTGTCTCCCG | AACCAGGCTC | 1560 |
| TGCCTGCACA | ATCTCCCAAA | GGCTGTAGAT | GACAAACAGC | TCAGAAAGCT | GCTGCTGAGT | 1620 |

-continued

| | | | | | | |
|---|---|---|---|---|---|---|
| GCTACTAGTG | GAGAGAAAGG | GGTGCGCATC | AAGGAGTGTA | GAGTGATGCG | AGACCTCAAA | 1680 |
| GGAGTTCATG | GGAACATGAA | GGGTCAGTCC | CTGGGCTACG | CCTTTGCGGA | GTTCCAAGAG | 1740 |
| CACGAGCATG | CCCTGAAAGC | CCTCCGCCTC | ATCAACAACA | ATCCAGAAAT | CTTTGGGCCT | 1800 |
| CTGAAGAGAC | CAATAGTGGA | GTTCTCTTTA | GAAGATCGAA | GAAAACTTAA | AATGAAGGAA | 1860 |
| TTAAGGATCC | AGCGCAGCTT | GCAAAAATG | AGATCCAAGC | CTGCAACTGG | TGAGCCTCAG | 1920 |
| AAGGGGCAAC | CAGAGCCTGC | AAAAGACCAG | CAACAGAAGG | CAGCTCAACA | CCACACAGAG | 1980 |
| GAACAAAGCA | AGGTGCCCCC | AGAGCAGAAG | AGAAAGGCGG | GCTCTACCTC | ATGGACCGGG | 2040 |
| TTCCAGACCA | AGGCTGAAGT | GGAGCAGGTG | GAGCTGCCTG | ATGGAAAGAA | GAGAAGAAAG | 2100 |
| GTCCTGGCGC | TCCCCTCACA | CCGAGGCCCC | AAAATCAGGT | TGCGGGACAA | AGGCAAAGTG | 2160 |
| AAGCCCGTCC | ATCCCAAAAA | GCCAAAGCCA | CAGATAAACC | AGTGGAAGCA | GGAGAAGCAG | 2220 |
| CAATTATCGT | CCGAGCAGGT | ATCTAGGAAA | AAAGCTAAGG | GAAATAAGAC | GGAAACCCGC | 2280 |
| TTCAACCAGC | TGGTCGAACA | ATATAAGCAG | AAATTATTGG | GACCTTCTAA | AGGAGCACCT | 2340 |
| CTTGCAAAGA | GGAGCAAATG | GTTTGATAGT | TGATGATGGC | AGCAGGCTGG | GTAAGAAGCT | 2400 |
| GGGTTGTATA | CTTTCTGGTG | ACACTCCTGG | GCTCCTCCCC | ATCCCCGTG | TCTCTCACTG | 2460 |
| AGGGAAAGAA | AATCCCCAAG | GGCACTGCCA | CTGTGCTCGG | AGGTGCCCTG | GACTGTGTAC | 2520 |
| ATCTGAACTT | TGGTCCATCC | TTTGATGTGT | GGTTCGTTAG | CCACAAAGAG | AAATATCTGA | 2580 |
| AAGTCAACAT | GATGCTTCTT | GCATATTATC | CAGATTATTG | TATGAAGTTG | TGTCTATAAT | 2640 |
| TATTACCAAT | TTTTATTCTT | TATTTCTCAA | ATGGAAACAC | CTGAAAAAGC | AAAAAAAAA | 2700 |
| AAAAAAAAA | CTCGAGGGGG | GCCCGTACCC | AAT | | | 2733 |

( 2 ) INFORMATION FOR SEQ ID NO:4:

( i ) SEQUENCE CHARACTERISTICS:
        ( A ) LENGTH: 2277 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| AUGGCUGGUC | UGACCCUGUU | CGUUGGUCGU | CUGCCGCCGU | CCGCUCGUUC | CGAACAGCUG | 60 |
| GAAGAACUGU | UCUCCCAGGU | UGGUCCGGUU | AAACAGUGCU | UCGUUGUUAC | CGAAAAAGGU | 120 |
| UCCAAAGCUU | GCCGUGGUUU | CGGUUACGUU | ACCUUCUCCA | UGCUGGAAGA | CGUUCAGCGU | 180 |
| GCUCUGAAAG | AAAUCACCAC | CUUCGAAGGU | UGCAAAAUCA | ACGUUACCGU | UGCUAAAAAA | 240 |
| AAACUGCGUA | ACAAACCAA | AGAAAAAGGU | AAAAACGAAA | ACUCCGAAUG | CCCGAAAAAA | 300 |
| GAACCGAAAG | CUAAAAAAGC | UAAAGUUGCU | GACAAAAAAG | CUCGUCUGAU | CAUCCGUAAC | 360 |
| CUGUCCUUCA | AAUGCUCCGA | AGACGACCUG | AAAACCGUUU | CGCUCAGUU | CGGUGCUGUU | 420 |
| CUGGAAGUUA | ACAUCCCGCG | UAAACCGGAC | GGUAAAAUGC | GUGGUUUCGG | UUUCGUUCAG | 480 |
| UUCAAAAACC | UGCUGGAAGC | UGGUAAAGCU | CUGAAAGGUA | UGAACAUGAA | AGAAAUCAAA | 540 |
| GGUCGUACCG | UUGCUGUUGA | CUGGGCUGUU | GCUAAAGACA | AAUACAAAGA | CACCCAGUCC | 600 |
| GUUUCCGCUA | UCGGUGAAGA | AAAAUCCCAC | GAAUCCAAAC | ACCAGGAAUC | CGUUAAAAAA | 660 |
| AAAGGUCGUG | AAGAAGAAGA | CAUGGAAGAA | GAAGAAAACG | ACGACGACGA | CGACGACGAC | 720 |
| GACGAAGAAG | ACGGUGUUUU | CGACGACGAA | GACGAAGAAG | AAGAAAACAU | CGAAUCCAAA | 780 |
| GUUACCAAAC | CGGUUCAGAU | CCAGAAACGU | GCUGUUAAAC | GUCCGGCUCC | GGCUAAAUCC | 840 |
| UCCGACCACU | CCGAAGAAGA | CUCCGACCUG | GAAGAAUCCG | ACUCCAUCGA | CGACGGUGAA | 900 |

```
GAACUGGCUC  AGUCCGACAC  CUCCACCGAA  GAACAGGAAG  ACAAAGCUGU  UCAGGUUUCC     960
AACAAAAAAA  AACGUAAACU  GCCGUCCGAC  GUUAACGAAG  GUAAAACCGU  UUUCAUCCGU    1020
AACCUGUCCU  UCGACUCCGA  AGAAGAAGAA  CUGGGUGAAC  UGCUGCAGCA  GUUCGGUGAA    1080
CUGAAAUACG  UUCGUAUCGU  UCUGCACCCG  GACACCGAAC  ACUCCAAAGG  UUGCGCUUUC    1140
GCUCAGUUCA  UGACCCAGGA  AGCUGCUCAG  AAAUGCCUGC  UGGCUGCUUC  CCCGGAAAAC    1200
GAAGCUGGUG  GUCUGAAACU  GGACGGUCGU  CAGCUGAAAG  UUGACCUGGC  UGUUACCCGU    1260
GACGAAGCUG  CUAAACUGCA  GACCACCAAA  GUUAAAAAAC  CGACCGGUAC  CCGUAACCUG    1320
UACCUGGCUC  GUGAAGGUCU  GAUCCGUGCU  GGUACCAAAG  CUGCUGAAGG  UGUUUCCGCU    1380
GCUGACAUGG  CUAAACGUGA  ACGUUCGAA   CUGCUGAAAC  ACCAGAAACU  GAAAGACCAG    1440
AACAUCUUCG  UUUCCCGUAC  CCGUCUGUGC  CUGCACAACC  UGCCGAAAGC  UGUUGACGAC    1500
AAACAGCUGC  GUAAACUGCU  GCUGUCCGCU  ACCUCCGGUG  AAAAGGUGU   UCGUAUCAAA    1560
GAAUGCCGUG  UUAUGCGUGA  CCUGAAAGGU  GUUCACGGUA  ACAUGAAGG   UCAGUCCCUG    1620
GGUUACGCUU  UCGCUGAAUU  CCAGGAACAC  GAACACGCUC  UGAAAGCUCU  GCGUCUGAUC    1680
AACAACAACC  CGGAAAUCUU  CGGUCCGCUG  AAACGUCCGA  UCGUUGAAUU  CUCCCUGGAA    1740
GACCGUCGUA  AACUGAAAAU  GAAAGAACUG  CGUAUCCAGC  GUUCCCUGCA  GAAAAUGCGU    1800
UCCAAACCGG  CUACCGGUGA  ACCGCAGAAA  GGUCAGCCGG  AACCGGCUAA  AGACCAGCAG    1860
CAGAAAGCUG  CUCAGCACCA  CACCGAAGAA  CAGUCCAAAG  UUCCGCCGGA  ACAGAAACGU    1920
AAAGCUGGUU  CCACCUCCUG  GACCGGUUUC  CAGACCAAAG  CUGAAGUUGA  ACAGGUUGAA    1980
CUGCCGGACG  GUAAAAAACG  UCGUAAAGUU  CUGGCUCUGC  CGUCCCACCG  UGGUCCGAAA    2040
AUCCGUCUGC  GUGACAAAGG  UAAAGUUAAA  CCGGUUCACC  CGAAAAAACC  GAAACCGCAG    2100
AUCAACCAGU  GGAAACAGGA  AAAACAGCAG  CUGUCCUCCG  AACAGGUUUC  CCGUAAAAAA    2160
GCUAAAGGUA  ACAAAACCGA  AACCCGUUUC  AACCAGCUGG  UUGAACAGUA  CAAACAGAAA    2220
CUGCUGGGUC  CGUCCAAAGG  UGCUCCGCUG  GCUAAACGUU  CCAAAUGGUU  CGACUCC      2277
```

( 2 ) INFORMATION FOR SEQ ID NO:5:

( i ) SEQUENCE CHARACTERISTICS:
        ( A ) LENGTH: 2277 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
ATGGCCGGCC  TGACCCTGTT  CGTGGGCCGC  CTGCCCCCCA  GCGCCCGCAG  CGAGCAGCTG      60
GAGGAGCTGT  TCAGCCAGGT  GGGCCCCGTG  AAGCAGTGCT  TCGTGGTGAC  CGAGAAGGGC     120
AGCAAGGCCT  GCCGCGGCTT  CGGCTACGTG  ACCTTCAGCA  TGCTGGAGGA  CGTGCAGCGC     180
GCCCTGAAGG  AGATCACCAC  CTTCGAGGGC  TGCAAGATCA  ACGTGACCGT  GGCCAAGAAG     240
AAGCTGCGCA  CAAGACCAA   GGAGAAGGGC  AAGAACGAGA  CAGCGAGTG   CCCCAAGAAG     300
GAGCCCAAGG  CCAAGAAGGC  CAAGGTGGCC  GACAAGAAGG  CCCGCCTGAT  CATCCGCAAC     360
CTGAGCTTCA  AGTGCAGCGA  GGACGACCTG  AAGACCGTGT  CGCCCAGTT   CGGCGCCGTG     420
CTGGAGGTGA  ACATCCCCCG  CAAGCCCGAC  GGCAAGATGC  GCGGCTTCGG  CTTCGTGCAG     480
TTCAAGAACC  TGCTGGAGGC  CGGCAAGGCC  CTGAAGGGCA  TGAACATGAA  GGAGATCAAG     540
GGCCGCACCG  TGGCCGTGGA  CTGGGCCGTG  GCCAAGGACA  AGTACAAGGA  CACCCAGAGC     600
```

| | | | | | | |
|---|---|---|---|---|---|---|
| GTGAGCGCCA | TCGGCGAGGA | GAAGAGCCAC | GAGAGCAAGC | ACCAGGAGAG | CGTGAAGAAG | 660 |
| AAGGGCCGCG | AGGAGGAGGA | CATGGAGGAG | GAGGAGAACG | ACGACGACGA | CGACGACGAC | 720 |
| GACGAGGAGG | ACGGCGTGTT | CGACGACGAG | GACGAGGAGG | AGGAGAACAT | CGAGAGCAAG | 780 |
| GTGACCAAGC | CCGTGCAGAT | CCAGAAGCGC | GCCGTGAAGC | GCCCCGCCCC | CGCCAAGAGC | 840 |
| AGCGACCACA | GCGAGGAGGA | CAGCGACCTG | GAGGAGAGCG | ACAGCATCGA | CGACGGCGAG | 900 |
| GAGCTGGCCC | AGAGCGACAC | CAGCACCGAG | GAGCAGGAGG | ACAAGGCCGT | GCAGGTGAGC | 960 |
| AACAAGAAGA | AGCGCAAGCT | GCCCAGCGAC | GTGAACGAGG | GCAAGACCGT | GTTCATCCGC | 1020 |
| AACCTGAGCT | TCGACAGCGA | GGAGGAGGAG | CTGGGCGAGC | TGCTGCAGCA | GTTCGGCGAG | 1080 |
| CTGAAGTACG | TGCGCATCGT | GCTGCACCCC | GACACCGAGC | ACAGCAAGGG | CTGCGCCTTC | 1140 |
| GCCCAGTTCA | TGACCCAGGA | GGCCGCCAG | AAGTGCCTGC | TGGCCGCCAG | CCCCGAGAAC | 1200 |
| GAGGCCGGCG | GCCTGAAGCT | GGACGGCCGC | CAGCTGAAGG | TGGACCTGGC | CGTGACCCGC | 1260 |
| GACGAGGCCG | CCAAGCTGCA | GACCACCAAG | GTGAAGAAGC | CCACCGGCAC | CCGCAACCTG | 1320 |
| TACCTGGCCC | GCGAGGGCCT | GATCCGCGCC | GGCACCAAGG | CCGCCGAGGG | CGTGAGCGCC | 1380 |
| GCCGACATGG | CCAAGCGCGA | GCGCTTCGAG | CTGCTGAAGC | ACCAGAAGCT | GAAGGACCAG | 1440 |
| AACATCTTCG | TGAGCCGCAC | CCGCCTGTGC | CTGCACAACC | TGCCCAAGGC | CGTGGACGAC | 1500 |
| AAGCAGCTGC | GCAAGCTGCT | GCTGAGCGCC | ACCAGCGGCG | AGAAGGGCGT | GCGCATCAAG | 1560 |
| GAGTGCCGCG | TGATGCGCGA | CCTGAAGGGC | GTGCACGGCA | ACATGAAGGG | CCAGAGCCTG | 1620 |
| GGCTACGCCT | TCGCCGAGTT | CCAGGAGCAC | GAGCACGCCC | TGAAGGCCCT | GCGCCTGATC | 1680 |
| AACAACAACC | CCGAGATCTT | CGGCCCCCTG | AAGCGCCCCA | TCGTGGAGTT | CAGCCTGGAG | 1740 |
| GACCGCCGCA | AGCTGAAGAT | GAAGGAGCTG | CGCATCCAGC | GCAGCCTGCA | GAAGATGCGC | 1800 |
| AGCAAGCCCG | CCACCGGCGA | GCCCCAGAAG | GGCCAGCCCG | AGCCCGCCAA | GGACCAGCAG | 1860 |
| CAGAAGGCCG | CCCAGCACCA | CACCGAGGAG | CAGAGCAAGG | TGCCCCCCGA | GCAGAAGCGC | 1920 |
| AAGGCCGGCA | GCACCAGCTG | GACCGGCTTC | CAGACCAAGG | CCGAGGTGGA | GCAGGTGGAG | 1980 |
| CTGCCCGACG | GCAAGAAGCG | CCGCAAGGTG | CTGGCCCTGC | CCAGCCACCG | CGGCCCCAAG | 2040 |
| ATCCGCCTGC | GCGACAAGGG | CAAGGTGAAG | CCCGTGCACC | CCAAGAAGCC | CAAGCCCCAG | 2100 |
| ATCAACCAGT | GGAAGCAGGA | GAAGCAGCAG | CTGAGCAGCG | AGCAGGTGAG | CCGCAAGAAG | 2160 |
| GCCAAGGGCA | ACAAGACCGA | GACCCGCTTC | AACCAGCTGG | TGGAGCAGTA | CAAGCAGAAG | 2220 |
| CTGCTGGGCC | CCAGCAAGGG | CGCCCCCCTG | GCCAAGCGCA | GCAAGTGGTT | CGACAGC | 2277 |

(2) INFORMATION FOR SEQ ID NO:6:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

| | | | | | | |
|---|---|---|---|---|---|---|
| GGGTTGCGGA | GGGTGGGCCT | GGGAGGGGTG | GTGGCCATTT | TTTGTCTAAC | CCTAACTGAG | 60 |
| AAGGGCGTAG | CGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACGCG | 300 |
| AAGAGTTGGG | CTCTGTCAGC | CGCGGGTCTC | TCGGGGGCGA | GGGCGAGGTT | CAGGCCTTTC | 360 |

| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:7:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| GGGTTGCGGA | GGGTGGGCCT | GGGAGGGGTG | GTGGCCATTT | TTTGTCCAAC | CCCAACTGAG | 60 |
| AAGGGCGTAG | GCGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACCGCG | 300 |
| AAGAGTTGGG | CTCTGTCAGC | CGCGGGTCTC | TCGGGGCGA | GGGCGAGGTT | CAGGCCTTTC | 360 |
| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:8:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

| GGGTTGCGGA | GGGTGGGCCT | GGGAGGGGTG | GTGGCCATTT | TTTGTCTAAG | CCTAAGTGAG | 60 |
| AAGGGCGTAG | GCGCCGTGCT | TTTGCTCCCC | GCGCGCTGTT | TTTCTCGCTG | ACTTTCAGCG | 120 |
| GGCGGAAAAG | CCTCGGCCTG | CCGCCTTCCA | CCGTTCATTC | TAGAGCAAAC | AAAAAATGTC | 180 |
| AGCTGCTGGC | CCGTTCGCCC | CTCCCGGGGA | CCTGCGGCGG | GTCGCCTGCC | CAGCCCCCGA | 240 |
| ACCCCGCCTG | GAGGCCGCGG | TCGGCCCGGG | GCTTCTCCGG | AGGCACCCAC | TGCCACCGCG | 300 |
| AAGAGTTGGG | CTCTGTCAGC | CGCGGGTCTC | TCGGGGCGA | GGGCGAGGTT | CAGGCCTTTC | 360 |
| AGGCCGCAGG | AAGAGGAACG | GAGCGAGTCC | CCGCGCGCGG | CGCGATTCCC | TGAGCTGTGG | 420 |
| GACGTGCACC | CAGGACTCGG | CTCACACATG | CAGTTCGCTT | TCCTGTTGGT | GGGGGGAACG | 480 |
| CCGATCGTGC | GCATCCGTCA | CCCCTCGCCG | GCAGTGGGGG | CTTGTGAACC | CCCAAACCTG | 540 |

( 2 ) INFORMATION FOR SEQ ID NO:9:

( i ) SEQUENCE CHARACTERISTICS:
        ( A ) LENGTH: 538 base pairs
        ( B ) TYPE: nucleic acid
        ( C ) STRANDEDNESS: double
        ( D ) TOPOLOGY: linear ( i i ) MOLECULE TYPE: cDNA (xi) SEQUENCE DESCRIPTION: SEQ ID NO:9:

```
GGGTTGCGGA  GGGTGGGCCT  GGGAGGGGTG  GTGGCCATTT  TTTGTCTACC  CTACTGAGAA   60
GGGCGTAGGC  GCCGTGCTTT  TGCTCCCCGC  GCGCTGTTTT  TCTCGCTGAC  TTTCAGCGGG  120
CGGAAAAGCC  TCGGCCTGCC  GCCTTCCACC  GTTCATTCTA  GAGCAAACAA  AAAATGTCAG  180
CTGCTGGCCC  GTTCGCCCCT  CCCGGGGACC  TGCGGCGGGT  CGCCTGCCCA  GCCCCCGAAC  240
CCCGCCTGGA  GGCCGCGGTC  GGCCCGGGGC  TTCTCCGGAG  GCACCCACTG  CCACCGCGAA  300
GAGTTGGGCT  CTGTCAGCCG  CGGGTCTCTC  GGGGGCGAGG  GCGAGGTTCA  GGCCTTTCAG  360
GCCGCAGGAA  GAGGAACGGA  GCGAGTCCCC  GCGCGCGGCG  CGATTCCCTG  AGCTGTGGGA  420
CGTGCACCCA  GGACTCGGCT  CACACATGCA  GTTCGCTTTC  CTGTTGGTGG  GGGGAACGCC  480
GATCGTGCGC  ATCCGTCACC  CCTCGCCGGC  AGTGGGGGCT  TGTGAACCCC  CAAACCTG    538
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 5..13
        (D) OTHER INFORMATION: /note= "Xaa represents isoleucine
            or leucine"

(xi) SEQUENCE DESCRIPTION: SEQ ID NO:10:

```
Glu  Ala  Ala  Thr  Xaa  Asp  Xaa  Pro  Gln  Gln  Gly  Ala  Asn  Lys
 1              5                        10
```

HUMAN TELOMERASE

INTRODUCTION

1. Field of the Invention

The field of this invention is an enzyme involved in cell replication.

2. Background

DNA at chromosome ends is maintained in a dynamic balance of loss and addition of telomeric simple sequence repeats. Sequence loss occurs during cell replication, in part from incomplete replication of chromosome termini by DNA-dependent DNA polymerase. Telomeric repeat addition is catalyzed by the enzyme telomerase: a ribonucleoprotein enzyme which uses a short region within the RNA as a template for the polymerase reaction. Although cells can maintain a constant number of telomeric repeats by balancing repeat loss and addition, not all cells do so. Human germline and cancer cells maintain a constant number of telomeric repeats, while normal human somatic cells lose telomeric repeats with each cycle of cell division. Cells which do not maintain stable telomere length demonstrate a limited proliferative capacity: these cells senesce after a number of population doublings correlated with the erosion of telomeres to a critical minimum length.

Because normal somatic cells do not appear to express or require telomerase and do not maintain chromosome ends, and because all or almost all cancer cells express high levels of telomerase activity and maintain chromosome ends, molecules that inhibit or alter telomerase activity could provide effective and non-toxic anti-cancer agents. Similarly, inhibition of telomerase in parasitic or infectious agents (e.g. trypanosomes, fungi, etc.) could provide a specific approach for reducing the viability or proliferation of these agents. Conversely, activation of telomerase in proliferation-restricted cells (such as normal somatic cells of the blood, vasculature, liver, skin, etc.) could provide a mechanism for promoting additional proliferative lifespan.

3. Relevant Literature

Purification of telomerase from the ciliate Tetrahymena and cloning of genes encoding two protein components of the enzyme is reported in Collins et al. (1995) Cell 81, 677–686 and copending U.S. patent application Ser. No. 08/359,125, filed 19 Dec. 1994. Literature relating to human telomerase include; Kim et al. (1994) Science 266, 2011–2014; and Feng et al. (1995) Science 269, 1236–1241. Literature relating to telomerase template modifications include Autexier et al. (1994) Genes and Devel 8, 563–575; Yu et al. (1991) Cell 67, 823–832; and Yu et al. (1990) Nature 344, 126–132. The Washington University-Merck EST Project contains an EST, reportedly deposited by Hillier et al. on Nov. 1, 1995, which has sequence similarity with the 3' end of SEQ ID NO:3, disclosed herein. For a general review, see Blackburn et al., Eds. (1995) Telomeres, Cold Spring Harbor Laboratory Press.

SUMMARY OF THE INVENTION

The invention provides methods and compositions relating to a human telomerase and related nucleic acids. Included are four distinct human telomerase subunit proteins, called p140, p105, p48 and p43 and telomerase protein domains thereof having telomerase-specific activity. The proteins may be produced recombinantly from transformed host cells from the subject telomerase encoding nucleic acids or purified from human cells. Also included are human telomerase RNA components, as well as specific, functional derivatives thereof.

The invention provides isolated telomerase hybridization probes and primers capable of specifically hybridizing with the disclosed telomerase gene, telomerase-specific binding agents such as specific antibodies, and methods of making and using the subject compositions in diagnosis (e.g. genetic hybridization screens for telomerase transcripts), therapy (e.g. gene therapy to modulate telomerase gene expression) and in the biopharrnaceutical industry (e.g. reagents for screening chemical libraries for lead pharmacological agents and nucleic acid polymerase reagents).

SEQ ID LISTING

SEQ ID NO: 1: p105 protein (amino acid sequence)
SEQ ID NO:2: p105 ambiguity maximized synthetic DNA
SEQ ID NO:3: p105 natural cDNA (the coding region is bp 97-2370)
SEQ ID NO:4: p105 E. coli optimized synthetic DNA
SEQ ID NO:5: p105 mammalian optimized synthetic DNA
SEQ ID NO:6: telomerase RNA
SEQ ID NO:7: telomerase RNA template region modification 1
SEQ ID NO:8: telomerase RNA template region modification 2
SEQ ID NO:9: telomerase RNA template region modification 3
SEQ ID NO:10 p43 peptide (XXXEAAT[I/L]D[I/L]PQQGANK, where the three X's are indeterminant residues)

DETAILED DESCRIPTION OF THE INVENTION

The invention provides isolated human telomerase proteins including human telomerase proteins p140, p105, p48 and p43, having molecular weights of about 149 kD, about 105 kD, about 48 kD and about 43 kD, respectively, as determined by polyacrylamide gel electrophoresis under denaturing conditions (Matsudaira and Burgess (1978) Anal Biochem 87, 386–396), and telomerase protein domains thereof. The telomerase proteins comprise assay-discernable functional domains including RNA recognition motifs and subunit binding domains and may be provided as fusion products, e.g with non-telomerase polypeptides. The human telomerase proteins of the invention, including the subject protein domains, all have telomerase-specific activity or function.

Telomerase-specific activity or function may be determined by convenient in vitro, cell-based, or in vivo assays: e.g. in vitro binding assays, cell culture assays, in animals (e.g. immune response, gene therapy, transgenics, etc.), etc. Binding assays encompass any assay where the molecular interaction of a telomerase protein with a binding target is evaluated. The binding target may be a natural intracellular binding target such as a telomerase subunit (e.g. another protein subunit or RNA subunit), a substrate, agonist, antagonist, chaperone, or other regulator that directly modulates telomerase activity or its localization; or non-natural binding target such a specific immune protein such as an antibody, or a telomerase specific agent such as those identified in assays described below. Generally, telomerase-binding specificity is assayed by telomere polymerase activity (see, e.g. Collins et al. 1995, Cell 81, 677–686), by binding equilibrium constants (usually at least about $10^7$ $M^{-1}$, preferably at least about $10^8$ $M^{-1}$, more preferably at least about $10^9$ $M^{-1}$), by the ability of the subject protein to function as negative mutants in telomerase-expressing cells, to elicit telomerase specific antibody in a heterologous host (e.g a rodent or rabbit), etc. In any event, the telomerase binding specificity of the subject telomerase proteins necessarily distinguishes ciliate telomerase, preferably distinguishes non-mammalian telomerases and more preferably distinguishes non-human telomerases. Exemplary telomerase proteins which are shown to have telomerase binding specificity include the telomerase RNA (e.g. SEQ ID NO:6) binding domains (e.g. RRM 1–4: SEQ ID NO:1, about residues 5–81, residues 115–192, residues 336–420, and residues 487–578, respectively), telomerase primer binding domains, nucleotide triphosphate binding domains and binding domains of regulators of telomerase such as nuclear localization proteins, etc. As used herein, a protein domain comprises at least 12, preferably at least about 20, more preferably at least about 40, most preferably at least about 80 residues of the disclosed respective SEQ ID NO.

The claimed human telomerase proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The telomerase proteins and protein domains may be synthesized, produced by recombinant technology, or purified from human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art. An exemplary method for isolating each of human telomerase protein p140, p105, p48 and p43 from human cells is as follows:

Several thousand (two to twelve thousand) liters of HeLa cells are grown in spinner culture. The cells are lysed by dounce homogenization in low-salt buffer to produce crude cell lysates. The lysates are supplemented with 15% glycerol and centrifuged at 125,000×g for 50 minutes to obtain a first soluble fraction enriched for telomerase activity (S-100 fraction). The S-100 fraction is adjusted to 0.2M ammonium sulfate, bound to SP Sepharose (Pharmacia), and developed with a gradient in sodium chloride, to obtain a second soluble fraction enriched for telomerase (SP fraction). The SP fraction is adjusted to about 0.3–0.4M ionic strength and bound to Q Sepharose (Pharmacia), and developed with a gradient in sodium chloride, to obtain a third soluble fraction enriched for telomerase (Q fraction). The Q fraction is adjusted to about 0.3–0.4M ionic strength, bound to phosphocellulose (Whatman), and developed with sodium chloride, to obtain a fourth soluble fraction enriched for telomerase (PC fraction). The PC fraction is adjusted to about 0.3–0.4M ionic strength, bound to 2'Omethyl RNA oligonucleotide immobilized on streptavidin agarose (Sigma), and eluted with a electrophoresis sample medium comprising 5% β-mercaptoethanol and 2% Sodium Dodecyl Sulfate to obtain a fifth soluble fraction (2'Omethyl fraction). The 2'Omethyl fraction is separated by polyacrylamide gel electrophoresis under denaturing conditions (Matsudaira and Burgess (1978) Anal Biochem 87, 386–396) to obtain gel protein bands at a molecular weight of about 140 kD, 105 kD, 48 kD or 43 kD having telomerase activity. The gel bands are excised or blotted to obtain purified human telomerase proteins p140, p105, p48 and p43.

The subject telomerase proteins find a wide variety of uses including use in isolating, enriching for and concentrating telomerase RNA and telomerase proteins, as immunogens, in the methods and applications described below, as reagents in the biotechnology industries, and in therapy. Recombinant telomerases are used in many applications where nascent oligonucleotides of predetermined sequence are desired. For example, native nucleic acid molecules are labeled or extended at their 3' ends by addition of a predetermined repeat sequence (for double-stranded oligonucleotides, both ends of the molecule may be tagged). Oligonucleotides complementary to the repeat are then used to amplify, sequence, affinity purify, etc. the nucleic acid molecules. The use of a repeat sequence for 3' end tagging improves specificity and provides sequence alternatives compared with non-templated enzymes presently available for this purpose, e.g. terminal transferase. Repeats encoding restriction enzyme sites provide repeat tagging to facilitate cloning and the use of telomerase alleviates the restrictive conditions required for optimal ligation with available ligase enzymes. Telomerase also finds use in regulating cell growth or increasing cell density tolerance; for example, cells contacted with an effective amount of exogenous telomerase to overcome the growth control limitation otherwise imposed by short telomere length. Telomerase may be introduced, expressed, or repressed in specific populations of cells by any convenient way such as microinjection, promoter-specific expression of recombinant enzyme, targeted delivery of lipid vesicles, etc. Advantageously, only a brief period of telomerase activity is required to allow many generations of continued proliferation of the contacted cell, due to the ability of telomerase to extend telomeres in one cell cycle by more sequence than is lost with each cell division.

The invention provides natural and non-natural human telomerase-specific binding agents including substrates, agonist, antagonist, etc., methods of identifying and making such agents, and their use in diagnosis, therapy and pharmaceutical development. For example, human telomerase-specific agents are useful in a variety of diagnostic and therapeutic applications. Novel human telomerase-specific binding agents include human telomerase-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate human telomerase function, e.g. human telomerase antagonists and find use methods for modulating the binding of a human telomerase or telomerase protein to a human telomerase binding target.

For diagnostic uses, the binding agents are frequently labeled, such as with fluorescent, radioactive, chemiluminescent, or other easily detectable molecules, either conjugated directly to the binding agent or conjugated to a probe specific for the binding agent. Binding agents also find use in modulating the telomerase activity present in a cell. For example, isolated cells, whole tissues, or individuals may be treated with a telomerase binding agent to activate, inhibit, or alter the specificity of telomerase assembly, localization, substrate interaction, or synthesis activity. Effectively treated cells have increased or decreased replication potential, or suffer from loss of proper telomere structure (resulting in lethality). These binding agents also find therapeutic use to control cell proliferation; for example, the uncontrolled growth of transformed cells (e.g. cancer cells) is managed by administration to the cells or patient comprising such cells of a telomerase binding agent which reduces telomerase activity. In contrast to many current chemotherapies, the present invention provides enhanced specificity of lethality, with minimum toxicity to dividing yet normal somatic cells.

The amino acid sequences of the disclosed telomerase proteins are used to back-translate telomerase protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural telomerase encoding nucleic acid sequences ("GCG" software, Genetics Computer Group, Inc, Madison Wis.). As examples, SEQ ID NO:2 discloses an ambiguity-maximized p105 coding sequence encompassing all possible nucleic acids encoding the full-length p105 protein. SEQ ID NO:3 discloses a natural human cDNA sequence encoding p105, SEQ ID NO:4 is a p105 coding sequence codon-optimized for $E.$ $coli$, SEQ ID NO:5 is a p105 coding sequence codon optimized for mammalian cell expression. Telomerase encoding nucleic acids may be part of human telomerase-expression vectors and may be incorporated into recombinant host cells, e.g. for expression and screening, transgenic animals, e.g. for functional studies such as the efficacy of candidate drugs for disease associated with human telomerase-mediated signal transduction, etc. Expression systems are selected and/or tailored to effect human telomerase protein structural and functional variants through alternative post-translational processing.

The invention also provides nucleic acid hybridization probes and replication/amplification primers having a human telomerase cDNA specific sequence contained in SEQ ID NO:3, bases 1–2345, and sufficient to effect specific hybridization thereto (i.e. specifically hybridize with SEQ ID NO:3, bases 1–2345 in the presence of natural ciliate telomerase cDNA, preferably in the presence of non-mammalian telomerase cDNA and more preferably, in the presence of murine telomerase cDNA). Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Human telomerase cDNA homologs can also be distinguished from other protein using alignment algorithms, such as BLASTX (Altschul et al. (1990) Basic Local Alignment Search Tool, J Mol Biol 215, 403–410).

The invention also provides non-natural sequence, recombinant and isolated natural sequence human telomerase RNA. Natural human telomerase RNA sequences include the nucleic acid disclosed as SEQ ID NO:6, or a fragment thereof sufficient to specifically hybridize with a nucleic acid having the sequence defined by SEQ ID NO:6 in the presence of a nucleic acid having the sequence disclosed in Feng et al. 1995, Science 269, 1236–1241. Such fragments necessarily distinguish the previously described (Feng et al. 1995, Science 269, 1236–1241) human RNA species. Preferred such fragments comprise SEQ ID NO:6, bases 191–210, bases 245–259, bases 341–369 or bases 381–399. Non-natural sequences include derivatives and/or mutations of SEQ ID NO:6, where such derivatives/mutations provide alteration in template, protein binding, or other regions to effect altered telomerase substrate specificity or altered reaction product (e.g. any predetermined sequence), etc.; see, e.g. Autexier et al., 1994, Genes & Develop 8, 563–575; Collins et al. (1995) EMBO J. 14, 5422–5432; Greider et al. (1995) Structure and Biochemistry of Ciliate and Mammalian Telomerases, in DNA Replication, DePamphlis, Ed., Cold Spring Harbor Laboratory Press. Additional derivatives function as dominant negative fragments which effectively compete for telomerase assembly. For examples, SEQ ID NO:7, 8 and 9 are derivatives which provide for modified substrate specificity and polymerase reaction product to interfere with cellular function (see, e.g. Hanish et al. (1994) Proc Natl Acad Sci 91, 8861–8865).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:3 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is immediately flanked by a sequence other than that which it is joined to on a natural chromosome. While the nucleic acids are usually RNA or DNA, it is often advantageous to use nucleic acids comprising other bases or nucleotide analogs to provide modified stability, etc. The subject nucleic acids find a wide variety of applications including use as translatable transcripts, hybridization probes, PCR primers, diagnostic nucleic acids, etc.; use in detecting the presence of human telomerase genes and gene transcripts and in detecting or amplifying nucleic acids encoding additional human telomerase homologs and structural analogs.

In diagnosis, human telomerase hybridization probes find use in identifying wild-type and mutant human telomerase alleles in clinical and laboratory samples. Mutant alleles are used to generate allele-specific oligonucleotide (ASO) probes for high-throughput clinical diagnoses. In therapy, therapeutic human telomerase nucleic acids are used to modulate cellular expression or intracellular concentration or availability of active telomerase. A wide variety of indications may be treated, either prophylactically or therapeutically with the subject compositions. For example, where limitation of cell growth is desired, e.g. neoproliferative disease, a reduction in telomerase expression is effected by introducing into the targeted cell type human telomerase nucleic acids which reduce the functional expression of human telomerase gene products (e.g. nucleic acids capable of inhibiting translation of a functional telomerase transcript). Conditions for treatment include various cancers, where any of a wide variety of cell types may be involved, restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

Telomerase inhibitory nucleic acids are typically antisense: single-stranded sequences comprising complements of the disclosed natural telomerase coding sequences. Antisense modulation of the expression of a given telomerase protein may employ telomerase antisense nucleic acids operably linked to gene regulatory sequences. Cell are transfected with a vector comprising a human telomerase sequence with a promoter sequence oriented such that transcription of the gene yields an antisense transcript capable of binding to endogenous human telomerase protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given human telomerase protein may be administered to the target cell, in or temporarily isolated from a host, at a concentration that results in a substantial reduction in expression of the targeted protein.

In other indications, e.g. certain hypersensitivities, atrophic diseases, etc., an increase in cell growth or proliferation is desired. In these applications, an enhancement in human telomerase expression is effected by introducing into the targeted cell type human telomerase nucleic acids which increase the functional expression of human telomerase gene products. Conditions for treatment include multiple sclerosis, where certain neuronal cells are involved, inflammatory disease states such as rheumatoid arthritis, where bystander cells are involved, transplant rejection where graft cells are involved, infectious diseases such as HIV infection where certain uninfected host cells are involved, or the like. Such nucleic acids may be human telomerase expression vectors, vectors which upregulate the functional expression of an endogenous human telomerase allele, or replacement vectors for targeted correction of human telomerase mutant alleles.

Various techniques may be employed for introducing of the nucleic acids into viable cells, e.g. transfection with a retrovirus, viral coat protein-liposome mediated transfection. The techniques vary depending upon whether one is using the subject compositions in culture or in vivo in a host. In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The invention provides methods and compositions for enhancing the yield of many recombinantly produced proteins by increasing maximum cell densities and survival time of host production cells in culture. Specifically, cultured cells are transfected with nucleic acids which effect the up-regulation of endogenous telomerase or the expression of an exogenous telomerase. For example, nucleic acids encoding functional human telomerase operably linked to a transcriptional promoter are used to over-express the exogenous telomerase in the host cell. Telomerase-expressing cells demonstrate enhanced survival ability at elevated cell densities and over extended culture periods.

The invention provides efficient methods of identifying agents, compounds or lead compounds for agents active at the level of a human telomerase modulatable cellular function. Generally, these screening methods involve assaying for compounds which modulate human telomerase interaction with a natural human telomerase binding target. A wide variety of assays for binding agents are provided including labeled in vitro telomere polymerase assays, protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc. Target cells also include progenitor cells for repopulating blood or bone marrow, tissue grafts, and tissue subject to degredation/high turnover such as digestive and vascular endothelia and pulmunary and dermal epithelia.

In vitro binding assays employ a mixture of components including a human telomerase protein, which may be part of multi-subunit telomerase, a fusion product with another peptide or polypeptide, e.g. a tag for detection or anchoring, etc. The assay mixtures comprise a natural intracellular human telomerase binding target, e.g. a substrate. While native binding targets may be used, it is frequently preferred to use portions (e.g. peptides, nucleic acid fragments) thereof so long as the portion provides binding affinity and avidity to the subject human telomerase conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the human telomerase specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the human telomerase and one or more binding targets is detected by any convenient way. For cell-free binding type assays, a separation step is often used to separate bound from unbound components. Separation may be effected by precipitation (e.g. TCA precipitation, inmmunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For telomere polymerase assays, binding is detected by a change in the polymerization by the telomerase of a nucleic acid or nucleic acid analog on the substrate.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the human telomerase protein to the target in the absence of the agent as compared with the binding affinity in the presence of the agent indicates that the agent modulates the binding of the human telomerase protein to the human telomerase binding target. Analogously, in the cell-based transcription assay also described below, a difference in the human telomerase transcriptional induction in the presence and absence of an agent indicates the agent modulates human telomerase-induced transcription. A difference, as used herein, is statistically significant and preferably represents at least a 50%, more preferably at least a 90% difference.

The following examples are offered by way of illustration and not by way of limitation.

EXAMPLES

1. Protocol for High-Throughput Human Telomere Polymerization Assay

A. Reagents:

Neutralite Avidin: 20 µg/ml in PBS.

human telomerase: $10^{-8}$–$10^{-5}$M human telomerase in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1 mM dATP, 1 mM dTTP, 1% glycerol, 0.5% NP-40, 50 mM BME, 1 mg/ml BSA, cocktail of protease inhibitors.

[$^{32}$P]α-dGTP 10xstock: 2>$10^{-5}$m "cold" dGTP with 100 µCi [$^{32}$P]α-dGTP. Place in the 4° C. microfridge during screening.

telomerase substrate: $10^{-7}$–$10^{-4}$M biotinylated telomerase substrate (5'-biotin-d(TTAGGG)$_3$-3') in PBS.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVo_3$ (Sigma # S-6508) in 10 ml of PBS.

B. Preparation of Assay Plates:

Coat with 120 µl of stock N Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 40 µl human telomerase (1–1000 fmoles/40 ul in assay buffer)

Add 10 µl compound or extract.

Add 10 µl [$^{32}$P]α-dGTP 10xstock.

Add 40 µl biotinylated telomerase substrate (0.1–10 pmoles/40 ul in assay buffer)

Shake at 25° C. for 15 minutes.

Incubate additional 45 minutes at 25° C.

Stop the reaction by washing 4 times with 200 µl PBS.

Add 150 µl scintillation cocktail.

Count in Topcount.

D. Controls for All Assays (Located on Each Plate):

a. Non-specific binding b. cold dGTP at 80% inhibition.

2. Protocol for High Throughput Human Telomerase Subunit-RNA Complex Formation Assay A. Reagents:

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{32}$P human telomerase protein 10xstock: $10^{-8}$–$10^{-6}$M "cold" human telomerase subunit (p105) supplemented with 200,000–250,000 cpm of labeled human telomerase (Beckman counter). Place in the 4° C. microfridge during screening.

Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVo_3$ (Sigma # S-6508) in 10 ml of PBS.

telomerase RNA: $10^{-7}$–$10^{-4}$M biotinylated RNA (SEQ ID NO:6) in PBS.

B. Preparation of assay plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-human telomerase protein (20,000–25,000 cpm/0.1–10 pmoles/well=$10^{-9}$–$10^{-7}$M final concentration).

Shake at 25° C. for 15 minutes.

Incubate additional 45 minutes at 25° C.

Add 40 µl biotinylated RNA (0.1–10 pmoles/40 ul in assay buffer)

Incubate 1 hour at room temperature.

Stop the reaction by washing 4 times with 200 µl PBS.

Add 150 µl scintillation cocktail.

Count in Topcount.

D. Controls for All Assays (Located on Each Plate):

a. Non-specific binding b. Soluble (non-biotinylated telomerase) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

5,770,422

What is claimed is:

1. An isolated protein comprising the amino acid of SEQ ID NO:1 or a functionally active fragment thereof.

2. The protein of claim 1, wherein said protein comprises the amino acid of at least one of SEQ ID NO:1, residues 5–81, 115–192, 336–420 and 487–578.

3. The protein of claim 1, wherein said protein comprises the amino acid of SEQ ID NO:1.

\* \* \* \* \*